United States Patent
Seibt et al.

(10) Patent No.: US 9,598,848 B2
(45) Date of Patent: Mar. 21, 2017

(54) SYSTEM AND METHOD FOR THE METERED DISPENSING OF A FRAGRANCE IN A CLOSED ROOM, IN PARTICULAR IN A LAVATORY OF A VEHICLE

(71) Applicant: Airbus Operations GmbH, Hamburg (DE)

(72) Inventors: Christian Seibt, Hamburg (DE); Jens Wiebalck, Hamburg (DE); Joerg Cremers, Hamburg (DE)

(73) Assignee: AIRBUS OPERATIONS GMBH, Hamburg (DE)

(*) Notice: Subject to any disclaimer, the term of this patent is extended or adjusted under 35 U.S.C. 154(b) by 0 days.

(21) Appl. No.: 14/943,839

(22) Filed: Nov. 17, 2015

(65) Prior Publication Data
US 2016/0145845 A1    May 26, 2016

(30) Foreign Application Priority Data
Nov. 21, 2014 (DE) .................. 10 2014 117 099

(51) Int. Cl.
| | | |
|---|---|---|
| *A61L 9/00* | (2006.01) | |
| *B01D 11/02* | (2006.01) | |
| *B01D 11/04* | (2006.01) | |
| *E03D 11/00* | (2006.01) | |
| *E03D 9/02* | (2006.01) | |
| *E03D 9/03* | (2006.01) | |
| *A61L 9/05* | (2006.01) | |
| *E03D 9/00* | (2006.01) | |

(52) U.S. Cl.
CPC ............... *E03D 9/031* (2013.01); *A61L 9/00* (2013.01); *A61L 9/05* (2013.01); *E03D 9/007* (2013.01)

(58) Field of Classification Search
CPC ... E03D 9/02; E03D 9/005; A61L 2/00; A61L 2/18
USPC ........... 422/5, 28, 255–256, 261; 4/222, 433
See application file for complete search history.

(56) References Cited

U.S. PATENT DOCUMENTS

2004/0133968 A1* 7/2004 Hoehne ................. B64D 11/02
                                                           4/233
2014/0157504 A1   6/2014 Witrington

FOREIGN PATENT DOCUMENTS

| AU | WO 01/90494 A1 * | 11/2011 | ............... E03D 9/03 |
|---|---|---|---|
| DE | 4134386 A1 | 4/1992 | |
| DE | 202005017056 U1 | 3/2007 | |
| EP | 0586826 A1 | 3/1994 | |
| EP | 1621961 A2 | 2/2006 | |
| WO | 0190494 A1 | 11/2001 | |

OTHER PUBLICATIONS

German Patent Office, German Search Report for German Patent Application No. 10 2014 117 099.7 mailed Aug. 10, 2015.

* cited by examiner

*Primary Examiner* — Monzer R Chorbaji
(74) *Attorney, Agent, or Firm* — Lorenz & Kopf, LLP.

(57) ABSTRACT

A system for the metered dispensing of a fragrance in a toilet, in particular in a lavatory of a vehicle, comprises a fragrance container having a fragrance stored in a receptacle, and a port carrying the fragrance and joined with the receptacle for guiding the fragrance out of the receptacle. The port is connectable with a flushing pipe for the toilet.

10 Claims, 1 Drawing Sheet

SYSTEM AND METHOD FOR THE METERED DISPENSING OF A FRAGRANCE IN A CLOSED ROOM, IN PARTICULAR IN A LAVATORY OF A VEHICLE

CROSS-REFERENCE TO RELATED APPLICATION

This application claims priority to German Patent Application No. 10 2014 117 099.7, filed 21 Nov. 2014, which is incorporated herein by reference in its entirety.

TECHNICAL FIELD

This relates to a system and a method for the metered dispensing of a fragrance in a toilet, a lavatory for a vehicle, as well as an airplane with such a lavatory.

BACKGROUND

Lavatories that are used by a large number of people, often are subject to elevated requirements on purity and hygiene. This relates not just to the cleanliness of surfaces and immaculate toilet fixtures, but also to the perceived odor. Known in the art is to install fragrance dispensers in lavatories, which are actuated permanently, periodically, controlled by motion sensors or via a tripping device coupled with the door. The disadvantage to these types of devices is the absence of any sensible metering, in particular for frequently used lavatories. In addition, the suitable location selected for dispensing fragrances with such a fragrance dispenser may prove inappropriate. Liquid fragrances are often sprayed in a room, and when frequently used may comprise a locally excessive concentration, with the concentration still being too low at the location where the undesired odor originated.

SUMMARY

The object of the embodiment is to propose a system for the metered dispensing of a fragrance in a lavatory or similarly closed rooms, which permits a suitable metering and/or improves the concentration at the location where undesired odors originate.

Proposed is a system for the metered dispensing of a fragrance in a toilet, in particular in a lavatory of a vehicle, which comprises a fragrance container with a fragrance stored in a receptacle, and a port carrying the fragrance and joined with the receptacle for guiding the fragrance out of the receptacle. The port is connectable with a flushing pipe for a toilet.

In addition, other objects, desirable features and characteristics will become apparent from the subsequent summary and detailed description, and the appended claims, taken in conjunction with the accompanying drawings and this background.

The fragrance container may be a container with any configuration desired, which comprises a receptacle suitable for storing a fragrance. By integrating a port joined with the receptacle, the fragrance may be siphoned out of the receptacle. The receptacle must be regarded as a space in which the fragrance is located, while the fragrance container is a higher-level unit that may also comprise a holder, ports for dispensing or receiving fragrances, or other devices.

The fragrance may be a liquid, a solid or a gaseous medium, or, as a mixture of liquids, comprise a dispersion, an emulsion, a solution or any other type of combination of several substances.

It would be advantageous if the fragrance may be made to exit the outlet or be readily conveyed through exposure to a gravitational force. Liquid fragrances may preferably comprise a relative low viscosity and contain scented oils. Solid fragrances may take the form of a powder, granulate, or tablets or other portionable units. While the fragrance is preferably a liquid fragrance, the embodiment is not limited thereto. The connection between the receptacle and port is here a liquid-carrying connection, i.e., a fluid connection.

The fragrance container may be designed as a rigid container, which should be able to balance out a diminishing volume of fragrance owing to repeated dispensing through the supply of ambient air. This may be realized by a corresponding check valve, for example, which automatically lets air into the receptacle during exposure to a vacuum. Alternatively, the container may also be given an elastic design, so that its shape collapses during repeated dispensing. For example, the receptacle could be realized in the form of a bag, which does not require that air be supplied to balance out the volume.

All receptacles share in common that they may preferably comprise a flange or some other connecting means, with which the fragrance container may easily be integrated into the system. Alternatively, a readily accessible inlet may be provided for refilling a fragrance. This may depend on the used dispensing device, as will be explained below.

The port is connectable with a flushing pipe of a toilet, so as to be placed in the toilet as needed exclusively when introducing a flushing liquid so as to dispense a fragrance. There are various options for removing solids and liquids from a toilet in a wastewater pipe or wastewater tank, in which a certain quantity of flushing water is always used. In buildings, removal takes place in particular by flushing with a relatively large quantity of flushing water, which carries all substances to the discharge of a toilet bowl, and from there into a wastewater pipe. In other embodiments, e.g., of the kind encountered in vehicles, removal takes place in particular through active siphoning or exposure to gravitational force, wherein a relatively small quantity of flushing water is used to support removal and dislodge substances adhering to the toilet bowl. This makes it possible to tangibly limit the size of both flushing water reservoirs and corresponding wastewater tanks. Nevertheless, both principles utilize a flushing pipe that is fluidically connected with a reservoir for flushing water, and situated downstream from a flushing valve. As the result of integrating the port on or in the flushing pipe, a metered quantity of fragrance is dispensed in a flushing water stream flowing through the flushing pipe in the flushing process, which then reaches the toilet bowl and there acts as a fragrance.

As a consequence, the system according to the embodiment permits an appropriate, metered dispensing of a fragrance to mask undesired odors directly at the location where they originate, wherein the appropriate metering clearly reduces the quantity of stored fragrance, which in particular diminishes the refilling frequency and prevents excessive metering and waste. In addition, introducing the fragrance into a flushing pipe tangibly increases the safety in a toilet employing the system according to the embodiment, since the fragrance is dispensed at a location not visible or accessible to the user, thereby preventing any influence. Furthermore, the system according to the embodiment may easily be integrated into an existing toilet, since only small modifications to the flushing pipe are required, but not to a main component of the toilet.

An advantageous embodiment comprises a dispensing device fluidically connected with the receptacle for the metered dispensing of a fragrance. The dispensing device may be designed in various ways, and must be able to reliably implement or initiate the removal of fragrance, both by way of passive and active components or assemblies, i.e., with an active conveyor or a device for initiating an automatic running or dispensing, without actively supplying mechanical power to the fragrance. Active dispensing devices may differ from each other depending on the form of the fragrance. For example, fluid-conveying dispensing devices may have a clearly different configuration than dispensing devices that convey solids. Since the specific embodiment of the dispensing equipment may be selected depending on existing boundary conditions, the type of dispensing equipment must not be construed as a limitation. An expert is able to also consider other types of dispensing equipment not described in any detail, which comprise a pressure tank, pumps or the like.

An especially advantageous embodiment comprises a control unit, which is coupled with the dispensing device and set up to actuate the dispensing device for dispensing a metered quantity of fragrance. The control unit may be a dedicated control unit or be integrated into an already existing control unit, for example which controls the individual components of the toilet, in particular in a vehicle toilet. In response to a signal triggered by a user at the press of a button, for example, such a control unit would perform a sequence of steps, which in particular encompass the actuation of components that cause flushing water to be introduced, a discharge valve to be opened, and the like. As a consequence, the dispensing of fragrance would have to be integrated into the sequence of steps induced by the existing control unit. For a dedicated control unit, it would be necessary to detect the signal triggered by the user, so that an appropriate dispensing process may be initiated.

An especially advantageous embodiment comprises an odor measuring device that may be secured in the room, wherein the control unit is connected with the odor measuring device, and set up to actuate the dispensing device for dispensing a metered quantity of fragrance depending on at least one odor detected by the odor measuring device. Integrating an odor measuring device provides a useful addition to the system according to the embodiment, wherein it involves a device for measuring odors with the use of suitable sensors that are able to detect specific odors. Suitable in particular are microelectronic gas sensors, which are tailored to specific gases or gas groups. These types of sensors are designed based on semiconducting metal oxides, based on electrically conducting polymers, or based on sensors that utilize a mass effect. The odor measuring device may here comprise in particular a group of sensors, so as to recognize various odors perceived as unpleasant by humans. For example, the control unit coupled with the odor measuring device may be set up to recognize various odors from the signals of the individual sensors based on a suitable algorithm. On the other hand, the individual sensors may also be connected with a dedicated control unit, which is used exclusively to recognize odors from the individual signals, and transmit the latter to the control unit in the form of data. It is also conceivable for the same odorants or the same odor-triggering molecule to be used so as to increase the reliability of different measuring principles.

The dispensing device may thus dispense a metered quantity of the fragrance in a targeted manner depending on at least one odor determined by the odor measuring device. In particular, the metering level may be determined based on the signal strength of the odor measuring device. This may be done by way of a linear correlation with a predetermined proportionality constant based up a reference table or a more complex dependency function, with which additional parameters apart from the determined odor may also be considered.

The odor measuring device may preferably be arranged separately from the dispensing device or from the outlet. As a result, odor recognition may take place in a location where a user of the room would also determine the odor, for example. The outlet from which the fragrance is dispensed is situated at the location where the odor originated. In this way, excessive fluctuations in the concentration of fragrance and the resultant smell may be prevented in the room. As a whole, the odor generated in the room is harmonized, and is not perceived by a user as being excessively unnatural or artificial, or too intensive.

It may be advantageous to introduce the metered quantity of fragrance into the flushing pipe only toward the end of the flushing process, so as to produce an especially long-lasting fragrance, and not to remove or flush the flow of fragrance from the toilet bowl. The system, which may use the same control unit for this purpose, that controls the dispensing device and/or is coupled with the odor measuring device, or even a standalone control unit, may in this case be set up to dispense the fragrance on a time delayed basis, wherein the time delay is achieved by observing a predetermined duration of the delay between when the flushing process was activated and the fragrance was dispensed, which in turn depends on the expected volume flow of the flushing water, as well as on the desired metering of the fragrance. The provided dosage of fragrance should have been completely dispensed by the end of the flushing process.

In an advantageous embodiment, the system comprises a delivery valve, which is situated underneath the receptacle, so that the fragrance designed in particular as a liquid fragrance flows through the port through exposure to a gravitational force as soon as the delivery valve has been opened. As a consequence, the system is technically very simple, but the function is still very reliable. The appropriate metering is initiated by the flow of flushing water in the flushing pipe. The potential energy of the liquid fragrance owing to the varying heights of the receptacle and port or delivery valve may increase the available pressure required for introducing a fragrance into the flushing water stream. The volume flow of the fragrance may be set by correspondingly dimensioning and/or actuating the delivery valve.

In another embodiment, the dispensing device may comprise a piston, which is movably guided in the receptacle, and determines the expansion of the fragrance in the receptacle. The term expansion here means the space taken up by the fragrance inside of the receptacle and toward the outlet. Moving the piston inside of the receptacle toward the fragrance makes it possible to exert a pressure on the latter, so that it is conveyed out of the receptacle by releasing a flow cross section. When utilizing such a dispensing device, use may also be made of a delivery valve or, in this instance, a stop valve. The piston and valve may be simultaneously actuated. If not desired, the siphoning out of fragrance may be prevented by closing the stop valve.

On the one hand, the piston may be moved or pressure may be exerted on the fragrance by introducing a pressurized fluid on a side of the piston opposite the fragrance. Controlled by a valve, pressurized air may conceivably be introduced into the receptacle on the side of the piston inside of the receptacle that bears no fragrance. In this way, the pressurized air generates a force that presses against the piston. The piston in turn presses against the fragrance, so that the latter may be dispensed by releasing a flow cross section, and the piston follows the movement of the fragrance.

An advantageous embodiment comprises a pre-loaded spring, which is situated in the receptacle, and presses against a side of the piston facing away from the fragrance. This embodiment is mechanically very simple, and may reliably exert a continuous, defined force on the fragrance under all environmental conditions.

As already mentioned above, the receptacle is connectable with a source for pressurized fluid on a side of the piston facing away from the fragrance. The source for pressurized fluid mayx be connected in the receptacle either continuously or as needed. Should a pressurized fluid become necessary for the function of a toilet component, a connection with the receptacle could be established at the same time that the respective component is triggered.

In another embodiment, the dispensing device comprises a Venturi nozzle, which is fluidically connected with the flushing pipe, so that flushing water flows through the Venturi nozzle. An insertion site may be introduced into a constricted location, and is to be fluidically connected with the port. This results in suction effect at the insertion site, which siphons the fragrance out of the fragrance container, and dispenses it directly into the flushing water stream. Also conceivable in this embodiment is to use a valve, which controls the fluidic connection with the port, and hence the admixing of the fragrance, at least from a chronological standpoint, and if necessary with respect to the desired volume flow as well.

The fragrance preferably comprises a natural scented oil or a mixture of several scented oils, so as to enhance the wellbeing of a user and preclude a health-impairing substance.

It is further conceivable that the fragrance comprise a cleaning agent, in particular when using a liquid fragrance. As a result, a contamination of the toilet bowl may continuously be prevented.

The embodiment further relates to a lavatory for a vehicle, comprising a toilet with a flushing pipe and a system for the metered dispensing of a fragrance in the toilet having the features specified above, wherein the dispensing device is set up to dispense the liquid fragrance into the flushing pipe.

The embodiment also relates to an airplane with at least one such lavatory.

Let it be noted at this juncture that the flushing pipe is connected in particular with a spraying ring, which dispenses flushing water into the toilet bowl via an at least partially annular outlet or via outlets or spray holes or spray nozzles distributed at least on a partial ring.

When using toilets that siphon under a vacuum, it may sometimes happen that solids or liquids get between the toilet bowl and a lining that envelops the toilet bowl during removal, so that contaminants may accumulate there over time, whose odors are at least partially offset or masked by the system according to the embodiment.

The embodiment further relates to a method for the metered dispensing of a fragrance in a toilet, in particular in a lavatory of a vehicle, comprising a fragrance container with a fragrance stored in a receptacle, and a port carrying the fragrance and joined with the receptacle for guiding the fragrance out of the receptacle, with the fragrance being supplied in a flushing pipe of the toilet.

The method may additionally encompass several variations or supplements. For example, the method in one advantageous embodiment may comprise a sequence of several steps, which are preferably linked with the removal process of the toilet, and may be initiated when a user presses a corresponding actuator button. In a first step, a (small) quantity of flushing water may be introduced into the toilet bowl, with which fragrance gets into the toilet bowl. After the materials in the toilet bowl have been siphoned away, more flushing water may be dispensed into the toilet bowl. These steps may be initiated by means of an aforementioned control unit, which is a control unit intended for general toilet functions, or a standalone control unit that is only coupled with an actuator button as well. The chronological sequence in which these steps are performed is completely open.

The method may be modified in such a way that the dispensing of flushing water is not or not only initiated by an actuator button. For example, the dispensing of flushing water may also be introduced by a door switch, which is coupled with a toilet door. As a result, the toilet would briefly flush and releases fragrance in the room in the process when the toilet door was opened. In this way, bad odors in the lavatory room may be prevented even given a prolonged nonuse of the toilet.

Let it be noted at this juncture that both a toilet flush lever and a door switch may be hooked up via a data system, a bus, a network or the like, for example by way of a CIDS (cabin information and data system).

BRIEF DESCRIPTION OF THE DRAWINGS

The various embodiments will hereinafter be described in conjunction with the following drawing figures, wherein like numerals denote like elements, and.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

Figure 1A:
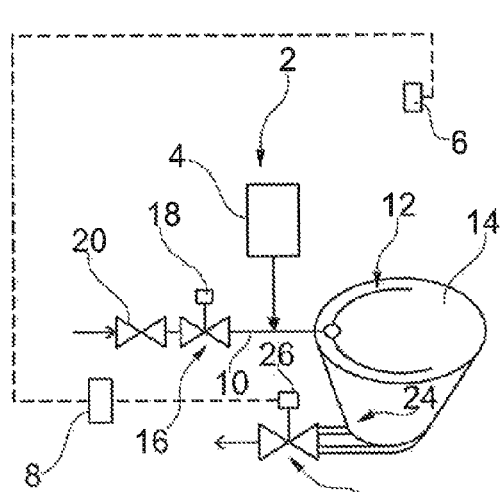
FIG. 1A shows a schematic depiction of an airplane toilet with integrated system for the metered dispensing of a fragrance.

FIG. 1A presents a system 2 for the metered dispensing of a fragrance in a toilet, in particular in a lavatory of an airplane. The system 2 comprises a fragrance container 4, an odor measuring device 6 and a controller 8, wherein a dispensing device is not shown on FIG. 1A in order to simplify the illustration. The fragrance container 4 is joined by the dispensing device (not shown) with a flushing pipe 10, which leads to a spraying ring 12 installed in the bowl of a toilet 14. The flushing pipe 10 is coupled upstream with a flushing valve 16, which is connected by an actuator 18 with the controller 8. Another check valve 20 situated further upstream prevents liquids from flowing back to a reservoir (not shown), a supply line or the like. A discharge valve 22 is in in turn connected with a discharge 24 of the toilet 14, and also comprises an actuator 26 joined with the control unit 8.

When flushing, the user presses a button, and a command from the control unit 8 correspondingly actuates the flushing valve 16, guiding a flushing liquid into the spray ring 12 via the flushing pipe 10. Subsequently, at the same time and/or thereafter, a vacuum is applied to the inside of the toilet 14 by actuating the discharge valve 22. All liquids or solids in the toilet 14 are conveyed out of the toilet 14 through the discharge 24.

Odors arising in the toilet 14 may be masked by admixing a fragrance located in the fragrance container 4, which in particular is a liquid fragrance comprising a scented oil or the like. Establishing a connection with the flushing pipe 10 causes the fragrance to be dispensed only as needed, which limits the required supply of fragrance, and prevents both an excessive metering and too high a fragrance concentration.

Fragrance metering may further be adjusted based upon an odor detected by the odor measuring device 6. As a result, more or less fragrance may be dispensed in the flushing process, as needed. Stronger odors in the lavatory in which the toilet is located may in this way be better masked or balanced out. Dispensing preferably takes place toward the end of the flushing process, in order to at least partially prevent the siphoning of liquid fragrance.

Figure 1B:
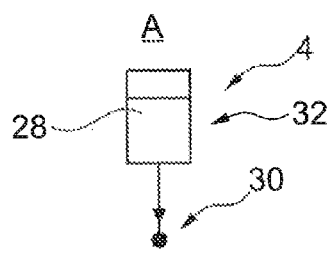
FIG. 1B shows schematic depictions of various dispensing devices.
Figure 1C:
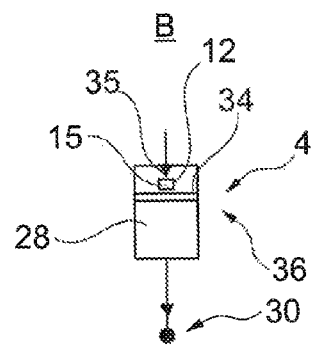
FIG. 1C shows schematic depictions of various dispensing devices.
Figure 1D:
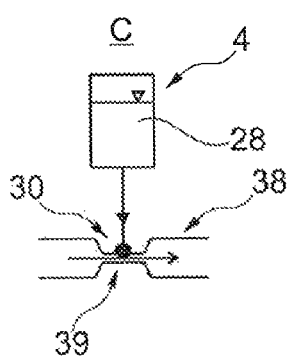
FIG. 1D shows schematic depictions of various dispensing devices.

FIG. 1B to 1d show various dispensing devices. FIG. 1B depicts a fragrance container 4 with a fragrance situated therein, which is designed as a liquid fragrance 28, which may be dispensed by a height difference through exposure to a gravitational force via a port 30 lying underneath the fragrance container 4 into the flushing pipe 10. Reference number 32 is used to label this dispensing device without active components, and points to the entire arrangement of the fragrance container 4 and port 30.

FIG. 1C shows a dispensing device 36. The system 2 is modified in such a way that the fragrance container 4 holding the fragrance designed as a liquid fragrance 28 incorporates a piston 34, which limits the expansion of the fragrance 28 in the fragrance container 4 at one surface via the overlying piston 34. By applying a pressurized fluid, for example compressed air, to the side of the piston 34 lying opposite the fragrance 28, the liquid fragrance 28 itself may be pressurized, so that it may thereby be dispensed. Alternatively or additionally, an actuator or pre-loaded spring 35 may exert a force on the piston 34, so that the liquid fragrance 28 is conveyed to the port 30.

The dispensing unit 38 shown on FIG. 1D is an injector in the form of a Venturi nozzle, which is connected with the port 30 at a constricted location 39. In particular a fragrance designed as a liquid fragrance 28 is siphoned out of the fragrance container 4 with flushing water as it flows through the Venturi nozzle 38, and admixed directly to the flushing water stream.

Figure 1E:
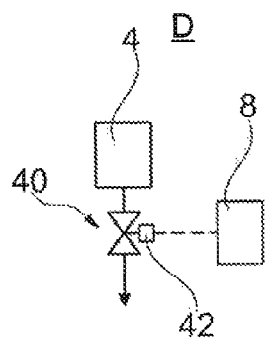
FIG. 1E shows a valve for opening or closing a flow cross section for conveying a fragrance stream.

All embodiments of the dispensing device may have allocated to them a valve 40 shown on FIG. 1E, which may be coupled with the control unit 8 via an actuator 42, and only dispenses the flushing water as needed.

Figure 2:
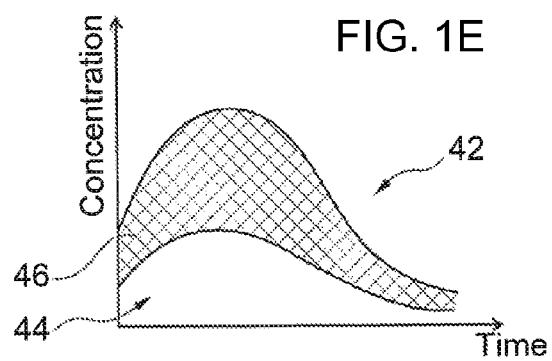
FIG. 2 shows a diagrammatic depiction of a dependency function between odors and fragrance metering.

FIG. 2 depicts an exemplary function 42 for metering the fragrance. The concentration of the fragrance 28 may be selected depending on the strength of the determined odor. The vertical (y) axis shows a concentration of the fragrance 28, while the horizontal (x) axis presents the chronological progression of fragrance dispensing. The lower curve includes the surface 44, and represents the determined odor inside the lavatory. As the odor intensifies, the fragrance dosage may be increased, as represented by the upper curve, wherein the distance from the lower curve represents the dosage of the fragrance 28. This area includes the surface 46, which is preferably proportional to the consumed quantity of fragrance 28.

Figure 3:
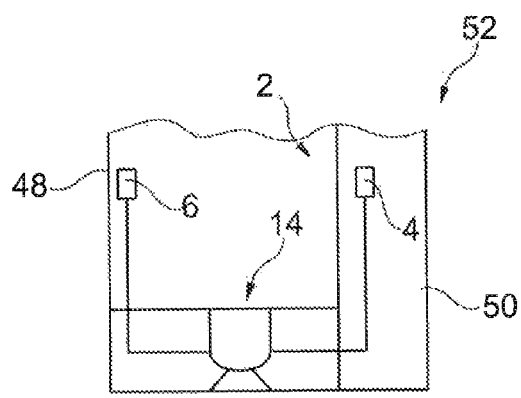
FIG. 3 shows a schematic view of a lavatory.

FIG. 3 exemplarily depicts a lavatory 52 of a vehicle with a toilet 14 installed therein, along with a system 2 according to the embodiment. A fragrance container 4 is here exemplarily installed in a service module 50, which is situated laterally inside the lavatory 52. An odor measuring device 6 may be secured to a wall 48 of the lavatory 52, and be connected with a control unit 8 not illustrated in this depiction.

In addition, let it be noted that "comprise" does not preclude any other elements or steps, and that "a" or "an" do not rule out a plurality. Let it further be noted that features described with reference to one of the above exemplary embodiments may also be used in combination with other features from other exemplary embodiments described above. Reference numbers in the claims are not to be regarded as a limitation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the embodiment in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the embodiment as set forth in the appended claims and their legal equivalents.

What is claimed is:

1. A system for the metered dispensing of a fragrance in a toilet, in particular in a lavatory of a vehicle, comprising:
   a fragrance container having a fragrance stored in a receptacle,
   a dispensing device for metered dispensing of the fragrance, the dispensing device connected with the receptacle;
   a control unit coupled to the dispensing device and configured to actuate the dispensing device for dispensing a metered quantity of the fragrance, wherein the control unit is couplable with a device for activating a flushing of the toilet;
   a port carrying the fragrance and joined with the receptacle for guiding the fragrance out of the receptacle, wherein the port is connectable with a flushing pipe for the toilet; and
   an odor measuring device that is securable in the lavatory, wherein the control unit is connected with the odor measuring device and is configured to actuate the dispensing device for dispensing the metered quantity of the fragrance depending on at least one odor determined by the odor measuring device.

2. The system of claim 1,
   wherein the system is set up to initiate the dispensing of the fragrance delayed by a predetermined time after starting the process of flushing the toilet.

3. The system of claim 1,
   further comprising a delivery valve, which is situated underneath the receptacle, so that the fragrance flows through the port through exposure to a gravitational force as soon as the delivery valve has been opened.

4. The system of claim 1,
wherein the dispensing device comprises a piston, which is movably guided in the receptacle, and determines space occupied by the fragrance in the receptacle.

5. The system of claim 4,
further comprising a pre-loaded spring, which is situated in the receptacle, and presses against a side of the piston facing away from the fragrance.

6. The system of claim 4,
wherein the receptacle is connected with a source for pressurized fluid on a side of the piston facing away from the fragrance.

7. The system of claim 1,
further comprising a Venturi nozzle, which is fluidly connected with the flushing pipe, and comprises an insertion site in a constricted location, which is fluidly connected with the port.

8. A method for the metered dispensing of a fragrance in a toilet, in particular in a lavatory of a vehicle, comprising a fragrance container with a fragrance stored in a receptacle, a dispensing device for metered dispensing of the fragrance, the dispensing device connected with the receptacle, a control unit coupled to the dispensing device and configured to actuate the dispensing device for dispensing a metered quantity of the fragrance, wherein the control unit is couplable with a device for activating a flushing of the toilet, a port carrying the fragrance and joined with the receptacle for guiding the fragrance out of the receptacle, in which fragrance is fed into a flushing pipe of the toilet, and an odor measuring device that is securable in the lavatory, wherein the control unit is connected with the odor measuring device and is configured to actuate the dispensing device for dispensing the metered quantity of the fragrance depending on at least one odor determined by the odor measuring device.

9. A lavatory for a vehicle, comprising:
a toilet;
a flushing pipe coupled to the toilet,
a fragrance container having a fragrance stored in a receptacle,
a dispensing device for metered dispensing of the fragrance, the dispensing device connected with the receptacle;
a control unit coupled to the dispensing device and configured to actuate the dispensing device for dispensing a metered quantity of the fragrance, wherein the control unit is couplable with a device for activating a flushing of the toilet;
a port carrying the fragrance and joined with the receptacle for guiding the fragrance out of the receptacle, the port connectable with the flushing pipe; and
an odor measuring device that is securable in the lavatory, wherein the control unit is connected with the odor measuring device and is configured to actuate the dispensing device for dispensing the metered quantity of the fragrance depending on at least one odor determined by the odor measuring device.

10. The lavatory of claim 9,
wherein the toilet comprises a spraying ring, which is connectable with the flushing pipe.

* * * * *